United States Patent [19]

Hatta et al.

[11] Patent Number: 4,744,359
[45] Date of Patent: May 17, 1988

[54] CAUTERY HEMOSTATIC UNIT

[75] Inventors: Shinji Hatta; Akira Taniguchi, both of Hachioji; Koichi Matsui, Tokyo; Takashi Tsukaya, Hachioji, all of Japan

[73] Assignee: Olympus Optical Co., Ltd., Tokyo, Japan

[21] Appl. No.: 22,473

[22] Filed: Mar. 6, 1987

Related U.S. Application Data

[63] Continuation of Ser. No. 774,618, Sep. 10, 1985, abandoned.

[30] Foreign Application Priority Data

Sep. 13, 1984 [JP] Japan .................. 59-192279
Nov. 28, 1984 [JP] Japan .................. 59-251236
Jun. 15, 1985 [JP] Japan .................. 60-130467

[51] Int. Cl.$^4$ .................................. A61B 17/38
[52] U.S. Cl. ...................... 128/303.1; 128/303.12; 219/497; 219/501

[58] Field of Search ............... 128/362, 398–401, 128/303.1, 303.12; 219/497, 499, 501

[56] References Cited

FOREIGN PATENT DOCUMENTS 58-69556 4/1983 Japan .

Primary Examiner—Lee S. Cohen
Assistant Examiner—David Shay
Attorney, Agent, or Firm—Armstrong, Nikaido, Marmelstein & Kubovcik

[57] ABSTRACT

This unit is for stopping hemorrhage by supplying a current for heating to a semi-conductive thermal element of small heat capacity to insure good heat response which is incorporated in the distal extremity of a slender probe, and possesses a means to recognize whether, or not, voltage fall between the both ends of the thermal element is within the permissible range in order to make it possible to detect qualitative deterioration of thermal element.

9 Claims, 5 Drawing Sheets

CAUTERY HEMOSTATIC UNIT

This application is a continuation of application Ser. No. 774,618, filed Sept. 10, 1985, now abandoned.

FIELD OF THE INVENTION AND RELATED ART

This invention is related to a cautery hemostatic unit having a means to detect the deterioration of the thermal element incorporated in the heater probe head.

In recent years, endoscopes which permit diagnosing and/or taking therapeutic measures in a deep region of the body, without incision from the external side of the body, by inserting a slender probe therein, have been used widely in various medical fields.

These endoscopes are designed so that an adequate medical instrument can be inserted into the hollow channel which pass therethrough in order to enable the taking of various therapeutic measures in addition to general observations.

By the way, a laser coagulator which irradiates laser beams to coagulate the bleeding site is used as a means to stop bleeding in such cases as removal of a tumor, etc., but the cost is expensive and use of such a device requires a great deal of skill and, besides, it is highly risky.

For such reasons, an instrument which uses a heater probe which can be delivered therethrough, and which permits coagulating the bleeding site, to which this heater probe is applied, by charging a heating coil, assembled in the distal extremity of this heater probe, with electricity has been developed.

However, the defect of such an instrument has been that the low heat response does not insure quick heating and subsequent cooling and, thereby, heat penetrates a lot into the surrounding tissues and tissues in other sites than the site to be treated are necrosed until the coagulation is achieved or until the probe is cooled after coagulation.

Therefore, as published in U.S. Pat. No. 4,449,528 and Japanese Patent Application Disclosure No. 69556/1983, there is a cautery hemostatic device using a thermal cautery probe (heater probe) made of a thermal element of good heat response to insure quick heating and subsequent cooling.

The above-mentioned prior art uses a Zener diode or electron avalanche diode as a thermal element, whereof the heat capacity is low (namely, the mass is small) and thereby the heat response is good to insure heating and cooling when the electric power that is supplied to the thermal element is turned on and off while minimizing tissue necrosis, and assures adequate coagulation at the required site.

However, because of an element of low heat capacity being used as a thermal element in order to assure good heat response, the consumption of electricity per unit time being very enormous, the temperature increasing very highly and the element being repeatedly used under severe conditions far over the rating, the deterioration of its property is unavoidable.

Consequently, after repeated use, the calorific value will be changed by the deterioration of the thermal element, and thereby the real calorific value will differ from the set value when used in practice to treat at the calorific value required according to the bleeding parts, and adequate treatment can not be expected.

And further deterioration will lead to the breakdown of the element during treatment and will cause unavoidable discontinuation of treatment or other troubles, which will affect confidence.

OBJECT AND SUMMARY OF THE INVENTION

The object of this invention is to offer a cautery hemostatic unit which permits detecting the deterioration of the property of the thermal element.

Another object of this invention is to offer a cautery heomstatic unit of high safety.

An additional object of this invention is to offer a cautery hemostatic unit which makes it possible to take adequate hemostatic measures.

This invention is an instrument that has a slender probe wherein a thermal element of low heat capacity and good heat response is incorporated, and that is used for stopping hemorrhage by supplying electric current for heating the thermal element, and that has such functions as differentiation of qualitative deterioration of the thermal element, etc. in order to enable adequate hemostatic measures to be taken in a very safe manner.

BRIEF DESCRIPTION OF THE DRAWINGS

In FIG. 1 is shown a block diagram illustrating the outline composition of the probe drive circuit.

In FIG. 2 is shown a circuit illustrating the concrete composition of the probe drive circuit.

In FIG. 3 is shown an oblique view of the appearance of the cautery hemostatic unit of this invention.

Other characteristics and advantages of this invention are going to be mentioned enough explained clearly in the following description.

DETAILED DESCRIPTION OF PREFERRED EMBODIMENTS

Figure 3:
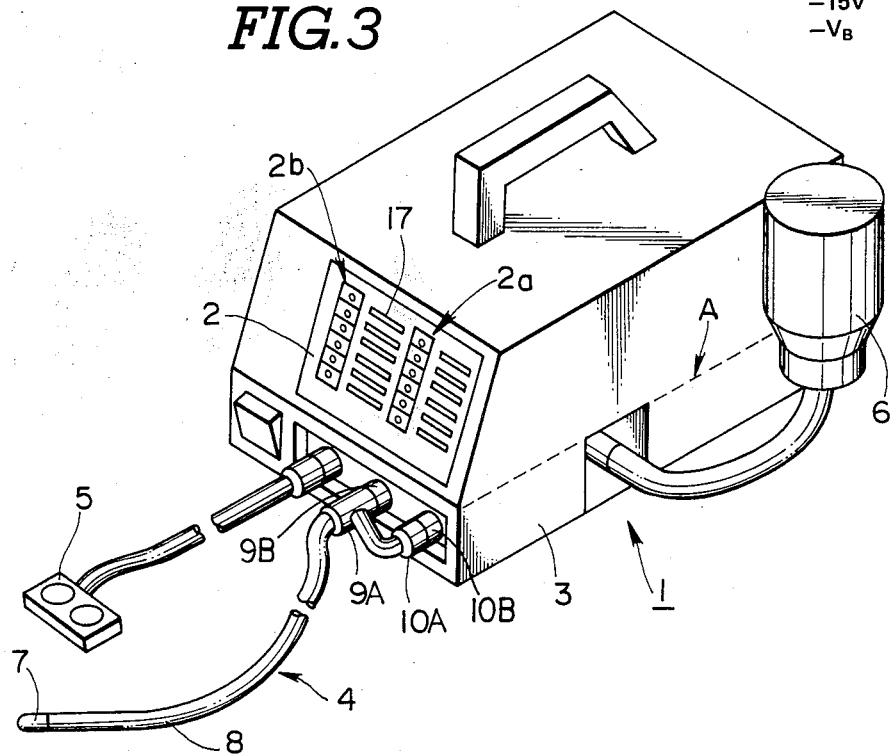

As shown in FIG. 3, the cautery hemostatic unit of the first embodiment is composed of a power box 3 whereof a slant panel 2 is installed on the front, a slender heater probe 4 which can be freely attached to or detached from the lower part of the front of this power box 3, a foot switch 5 which can be freely connected to or disconnected from the power box 3 by the use of a connector, and a water feed tank 6 which is mounted at one side.

The heater probe 4 incorporates a coaxial cable channel to supply electricity through a narrow-diametered, flexible probe 8 which can be delivered through a hollow channel of an endoscope (not illustrated) to a thermal element assembled in the distal extremity 7 thereof, and a water channel to feed washing water.

By connecting the electricity connector 9A and the water feed connector 10A of the proximal side of the heater probe 4 to the connector receptacles 9B and 10B, respectively, of the power box 8 and by connecting the connector of the foot switch 5 to the power box 3, washing water in the water tank 6 can be supplied through the water channel and jetted out forward to the affected part from the nozzle of the extremity 7 of the heater probe 4 to wash it, when the water feed (washing) switch side of the foot switch is pushed, and the thermal element can be heated via the coaxial cable 5 when the heat switch side of the foot switch 5 is pressed.

The jet amount of the above-mentioned washing water and the heating amount of the thermal element can be selectively set according to the affected part by the use of the setting buttons 2a and 2b on the panel 2.

The power box 3, incorporating an electric system and a water feed system, is designed so that it can be easily assembled as a complete unit by assembling these two systems separatedly, for example, as illustrated in FIG. 3, by placing an intermediate chassis at the position indicated by a dotted line in order to separate the electric system in the upper portion from the water feed system in the lower portion, and by installing a water pump in a water-proof frame in order to maintain safety.

Figure 1:
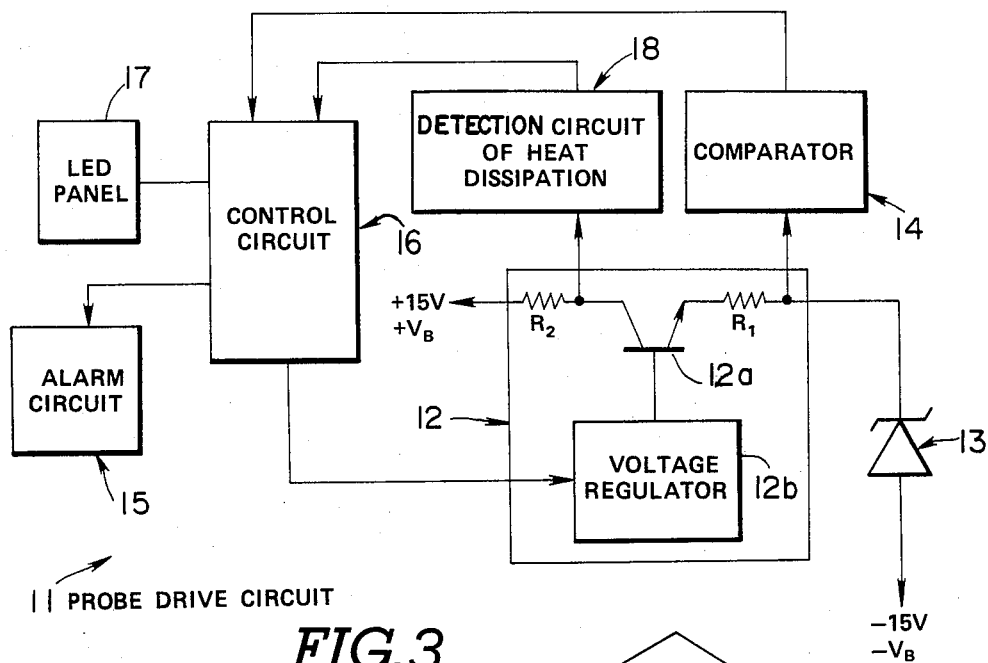
FIGS. 1, 2 and 3 are related to a first embodiment.

The composition of the main part of the electricity system includes a function to detect the deterioration of a probe (called probe drive circuit) and is shown in FIG. 1.

The probe drive circuit 11 consists of a constant current circuit 12, a zener diode 13 as a thermal element of good heat response whereto constant current is supplied from the constant current circuit 12, a comparator circuit 14 which detects for example, the cathode side voltage of the Zener diode 13 and compares it with a reference voltage, a control circuit 16 which receive the discriminating output from this comparator circuit 14 and keeps the thermal element working or operates the alarm circuit 15 which warms of the deterioration, and a heat dissipation detection circuit 18 which detects the heat dissipation set on the LED panel 17.

The above-mentioned control circuit 16 does not detect the output from the comparator circuit 14 simultaneously with conduction of electricity to the Zener diode 13, but does so, for example, 50 msec after electric current begins to flow. This is for waiting until stabilization of voltage and for descrimination after heating the Zener diode 13 to the proper temperature for use or to a temperature near it.

The above-mentioned control circuit 16 has a control function related to the descrimination of deterioration of the Zener diode 13 and, in addition, has functions such as turning on or off the LED panel 17 according to the operations set with buttons 2a and 2b on the above-mentioned panel 2, the controlling and setting the time-constant parameter of the heat dissipation detect circuit 18 according to the set operations.

The above-mentioned Zener diode 13 is made of a material, for example, whereof Zener voltage $V_z$ is about 20 V and the rating is 5 W. The anode of this Zener diode 13 is connected to the negative power supply end $-V_B$ ($V_B=15$ V) of the constant current circuit 12 and the cathode thereof is connected to the emitter of the control transistor 12a of the constant current circuit 12 via the resistance $R_1$. A fixed resistance and a variable resistance are incorporated in the probe 4 in order to enable setting of a current value where the current value is equivalent to the required heat amount and the limit current value, even when the Zener voltage of the Zener diode 13 varies, and the amount of current can be thus adjusted easily.

Figure 2:
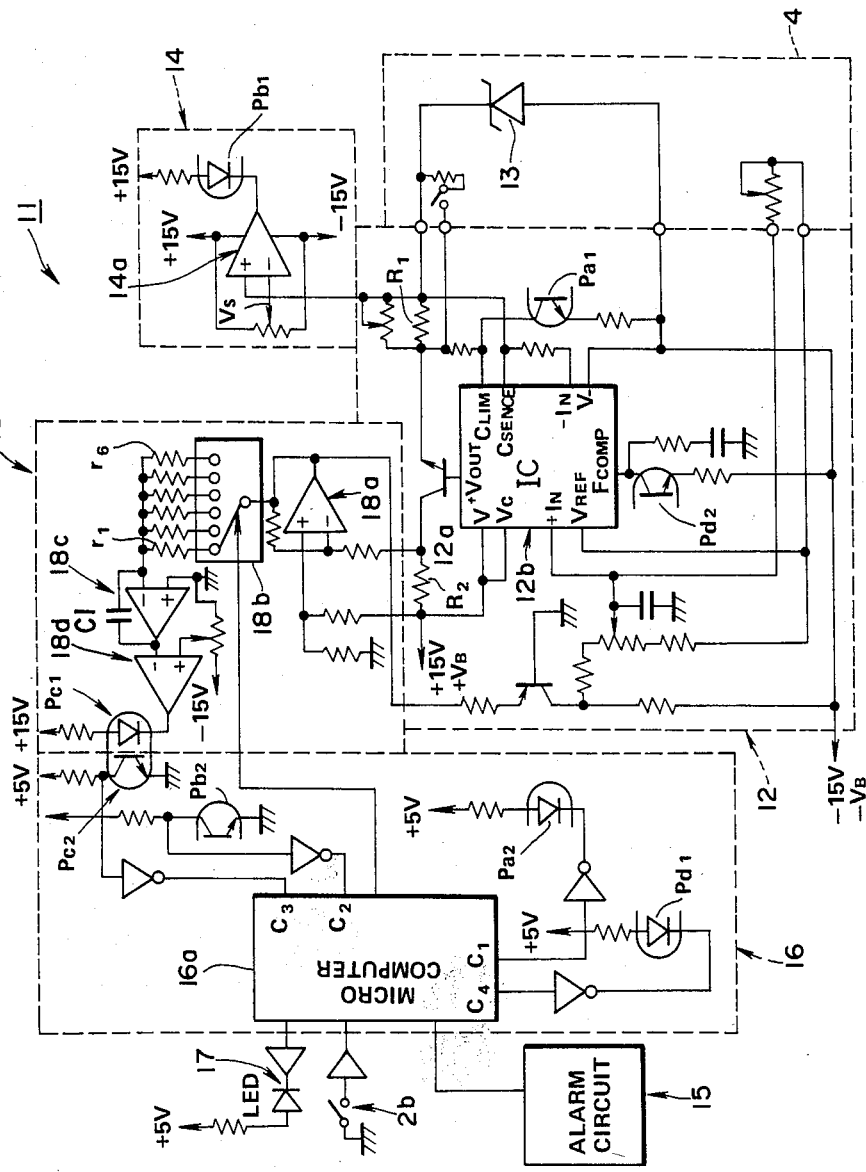

In the above-mentioned constant current circuit 12, a constant voltage IC ($\mu$A 723) 12b is used, for example, as shown in FIG. 2. By the IC 12b, the collector emitter current of the control transistor 12a is controlled at a fixed current value, for example, 530 mA. Consequently, the power consumption in the Zener diode 13 is : 20 V$\times$0.53 A$=$10.6 W, and this diode is used under conditions which exceed its rating. The heat capacity of the distal extremity 7 wherein the Zener diode 13 is incorporated is small enough, even including the heat capacity of Zener diode 13, and is heated to a high temperature rapidly as soon as the diode 13 is charged with electricity. Therefore, the Zener diode 13 is also used under conditions which exceed the maximum rating for its environmental temperature.

The above-mentioned constant voltage IC 12b is equipped with a current limit terminal $C_{LIM}$ that permits limiting the maximum value of output current and releasing the limit of the output current when electricity is supplied to photo-transistor $P_{a1}$ which forms a photo coupler, and light emitting diode $P_{a2}$ which forms the other half of this photo coupler is controlled to be turned on or off by a signal output from terminal $C_1$ of a one chip microcomputer (shortened as MC) which forms control circuit 16.

In FIG. 2 is shown the comparator circuit 14 that detects the deterioration of the above-mentioned Zener diode 13, wherein the non-reverse input terminal of the comparator 14a is connected to the cathode of Zener diode 13 and the standard voltage Vs is impressed at the reverse input terminal, and, for example, a voltage in the range from $-15$ V to $+20$ V may be set as this standard voltage Vs. Consequently, in the normal condition that Zener diode 13 is not deteriorated, the output from comparator 14a is non-reverse and light emitting diode $P_{b1}$, of a photo coupler connected to the output terminal does not light and consequently, photo transistor $P_{b2}$, the companion to this diode, is not turned on and terminal $C_2$ of MC 16a is maintained at a low level. Zener diode 13 is thus used repeatedly and, subsequently, its property is deteriorated, and when its Zener voltage decreased below 20 V, this is detected and the comparator 14a outputs a deterioration signals as a reverse output, light emitting diode $P_{b1}$ lights, the photo transistor $P_{b2}$, companion to light emitting diode $P_{b1}$, is turned on, the terminal $C_2$ is set at high level and, by this deterioration signal, MC 16a outputs a signal to alarm circuit 15 to turn it on to give the alarm of deterioration to the user. (Following such an alarm, it is possible to light light emitting diode $P_{d1}$ and turn on photo transistor $P_{d2}$ of constant current circuit 12, by outputting a high-level signal from the termianl $C_4$, in order not to output current to the Zener diode 13. Of course, this system may be used only for an alarm without this additional operation).

Now, in order to detect that the set value has been reached when the heat generation quantity (more precisely, the conduction quantity) is set by the setting button 2b of panel 2, the following arrangements are made: When the voltage across the resistor $R_2$ on the collector side of transistor 12a for controlling the constant current circuit 12 reaches the prescribed conduction quantity (value) through buffer 18a, further through multiplexer 18b and by way of integration circuit 18 which as been set by the time constant of a resistance selected from resistance $r_1, \ldots, r_6$ and the capacitance of capacitor C1 the higher voltage signal inverts the output of comparator 18d to put out light emitting diode $P_{C1}$ and to shut off photo-transistor $P_{C2}$ which forms a photodiode pair with said light emitting diode $P_{C1}$, and when these high level signals are input to terminal $C_3$ of microcomputer 16a through the inverter, the microcomputer 16a causes, through its terminal $C_4$, the light emitting diodes $Pd_1$ to emit light, the phototransistor $Pd_2$ of the constant current circuit 12 is caused to conduct, and the current supplied to the Zener diode 13, is shut off.

The above-mentioned multilexer 18b is controlled by an output signal from MC 16a and this output signal is formed according to the content of the operation set with the setting button 2b on the panel 2. In FIG. 2, only a single control line is used, but as an alternative method, it is also possible to cause the 3-bits signal output from microcomputer 16a to select the number of serial resistances out of a serial connection (not a parallel connection as shown in the figure), so that time constant can be variably set.

When light emitting diode $Pd_1$ lights, photo transistor $Pd_2$ is turned on and the current is cut off and, simultaneously, by a not-illustrated photo coupler, the condenser C1 of intergrator 18c is reset.

The operation in the first embodiment thus composed is as follows. When bleeding occurs at an affected site in treatment thereof, it is operable to wash the affected part by pushing the water feed foot switch 5 after setting the water feed button 2a at an adequate value. The amount of water feed is set and controlled by MC 16a. The heating current amount suitable for the affected part is selected by the use of heat amount setting button 2b, and a fixed current is supplied to the Zener diode 13, incorporated in the distal extremity 7 of the heater probe 4, by pushing the electricity supply switch while applying the distal extremity 7 of heater probe 4 to the affected part, and the Zener diode is heated very rapidly thereby. The heat capacity of the distal extremity 7 is very small, and it is therefore heated at a high-speed following electricity supply and blood of the bleeding part whereon the distal extremity 7 is applied and is coagulated by the heat. By selecting the setting buttons 2b, the multiplexer 18b is connected electrically with one of the resistances r1–r6 which corresponds thereto via MC 16a and IC 18c is set at a required time constant, and, when the above-mentioned Zener diode 13 is charged with electricity, the IC 18c begins to integrate. When the current amount reaches the set value, the output of the comparator 18d is reversed, light emitting diode $Pc_1$ lights and the current to photo transistor $Pc_2$ is cut off. This signal is thus input in MC 16a, and for example, the output from terminal $C_4$ makes light emitting diode $Pd_1$ light, supplies electricity to photo transistor $Pd_2$ of constant current circuit 12, and cuts off the current to the Zener diode 13. This signal makes the buzzer function and permits the user to confirm the current supply.

When the above-mentioned current supply is stopped, the temperature of the distal extremity 7 that incorporates Zener diode 13 falls largely by heat conduction with a small heat loss because of the very small heat capacity thereof and, therefore, the temperature of the distal extremity 7 decreases to that of tissue around the affected part. In short, subsequently to stopping current to the distal extremity 7, it is rapidly cooled together with surrounding tissue. Therefore, after blood is coagulated and bleeding is stopped, the cooling rate is rapid and, thereby, tissues other than the tissue whereto the distal extremity 7 is applied are not heated to high temperature and it is possible to prevent the tissue surrounding the affected part from necrosis.

The above-mentioned Zener diode 13 is made of a material having as small heat capacity as possible, namely a material of small mass, and is used at a power output that is far over its rating, and the repeated use thereof causes a gradual decrease in Zener voltage Vz. So, when the Zener voltage Vz decreases, for example, below 20 V, the comparator circuit 14 detects this phenomenon, light emitting diode $Pb_1$ lights by the reverse output as a result of detection of deterioration, photo transistor $Pb_2$ which is the companion thereto is turned on and this detector output is received by MC 16a, for example, 50 msec later. Thus, following the input of this detection signal, MC 16a makes the alarm circuit 15 work and it signals that the Zener diode 13 is deteriorated. In order to avoid the use of it under such a condition, MC 16a outputs a high-level control signal from the terminal $C_4$, lights light emitting diode $Pd_1$ via the inverter, and turns on photo transistor $Pd_2$ of constant current circuit 12 and consequently breaks the current to the Zener diode 13.

When the detection of deterioration is set so that the deterioration of Zener diode 13 can be detected at its early stage, the detection output can be arranged to make only the alarm circuit work in order to alarm the user to replace the diode as soon as possible. Therefore, if it is examined whether it will be necessary to replace heater probe 4 or Zener diode 13 by setting a standard voltage which permits detecting the deterioration that enables treatment once or several times, for example, under usual conditions and by driving before use, then deterioration which requires replacement during treatment need not be detected and the necessity of discontinuing the treatment will be avoided.

It is also possible to compose the comparator circuit 14 of two comparators set at different standard voltages $V_{Z1}$ and $V_{Z2}$, one of which detects the early stage of deterioration (in this case, $V_{Z1} > V_{Z2}$) and the other, more advanced stage of deterioration, so that the former makes the alarm circuit 15 work by outputting a deterioration signal thereto and power supply to Zener diode 13 is stopped when a deterioration signal is output from the latter. Furthermore, it is possible to use three comparators in combination as a compare circuit in order to be able to detect the early, intermediate and late stages of deterioration and to take adequate measures.

In the above-mentioned MC 16a is used in the control circuit 16, but it is also possible, without using it, to drive the alarm circuit 15 directly, for example, with an output from the comparator circuit 14 and to break the current of the constant current circuit 12 through the intermediary of a photo coupler. In the same way, when the amount of current reaches the set level, it is also possible to turn on the light emitting diode $Pc_1$ and to break the current by installing photo transistor $Pd_2$ of the constant current circuit 12 on the side of MC 16a instead of using photo transistor $Pc_2$, the companion to this diode $Pc_1$.

The setting button 2b may be used to turn on the corresponding LED directly or to control directly the selection of conduction terminals of the multiplexer 18b.

Any constant current circuits of different circuit compositions that have been known can be used for this invention as constant current circuit 12.

In addition to Zener diode 13 any diode that utilizes electron avalanche such as an avalanche diode, etc. can be used as the thermal element of this invention. Not only with such types of diodes but also with general diodes or semi-conductors such as transistor, etc. or semi-conductive elements including a thermistor, etc., that function similarly are also available.

In case of delay in recognition of deterioration from current conduction without using MC 16a, this delay is available by installing an analog switch, which functions according to the output from the integrator, on the side of the comparator 14a, for example, as illustrated in FIG. 2, in order to make this integrator work at the time when electricity is supplied thereto, and by setting it so that current is conducted to the analog switch when the integrator output reaches a certain level or higher. (This "certain level" can be set more exactly by comparing with a comparator). The delay function is also available by delaying current conduction on the side of alarm circuit 15.

Even in a case that the recognition output is normal, it is also possible to run on, for example, a LED, etc. in order to inform the user that the thermal element works normally.

As an alarm circuit 15 that functions according to recognition of an output informing of the deterioration of the thermal element, it is possible to use auditory means such as a buzzer, etc. or visual means such as a LED which as a remarkable color light, etc. or to use these two means in combination.

A semi-conductive element of as small heat capacity as possible, to insure rapid heating and subsequent cooling, is preferred as the above-mentioned semi-conductive element, and, therefore, it is generally used under a condition that electricity output is far over the rating or that the environmental temperature exceeds the rating, but it is possible that, according to the affected parts or the type of thermal element, the semi-conductive element may be used under condition with its rating.

The recognition of deterioration is not necessarily delayed from the time of current conduction to the thermal element.

This invention is not limited to the case wherein the heater probe is delivered through a channel in an endoscope.

This invention can be used not only for hemostasis but also for bactericial treatment by heating, etc.

As mentioned up to here, in the first embodiment, the invention has means to detect deterioration of a thermal element and, therefore, when the property of the thermal element is deteriorated, an alarm circuit works and the user can take adequate measures for replacement of the heater probe or thermal element, etc. Consequently, it is possible to avoid the use under such an unsuitable condition that the heat amount differs from the set value due to deterioration of the property or that the reliability has decreased.

Figure 4:
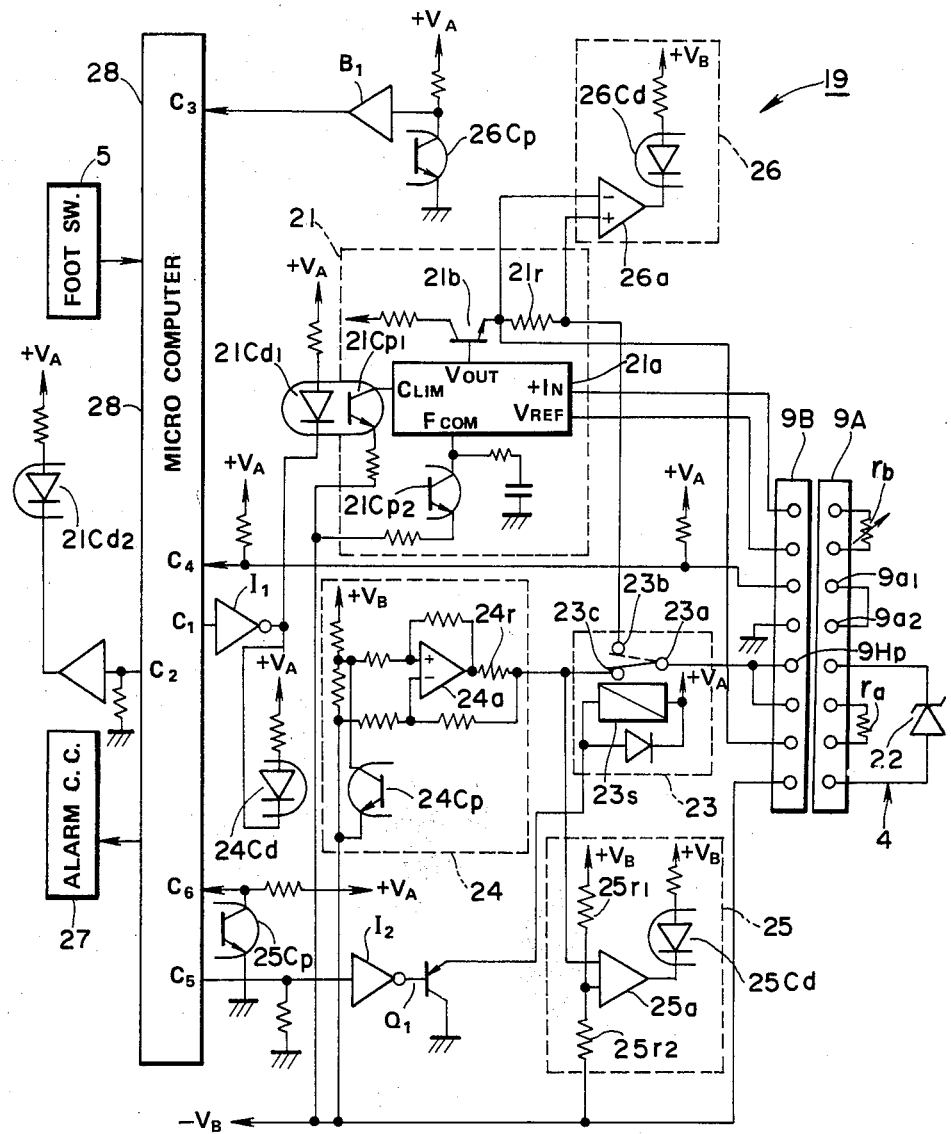
In FIG. 4 is shown a block diagram illustrating the probe drive circuit in a second embodiment.

FIG. 4 shows the probe drive circuit 19 in the second embodiment of this invention.

The probe drive circuit 19 is composed of a constant current circuit 21, a Zener diode 22 as a thermal element whereto a constant current is supplied from the constant current circuit 21, a minute (small) constant current circuit 24 that supplies a minute constant current (ex. 10 mA) to the Zener diode 22 through the intermediary of relay 23 for detecting qualitative deteriortion of the above-mentioned Zener diode 22, a short-circuit deterioration detects circuit 25 that detects property deterioration as to whether the cathode potential is above the set level or not, or presence or absence of a short-circuit, under condition that this minute constant current runs, a broken wire detect circuit 26 that detects whether, or not, the wire of the heater probe 4 is broken, an alarm circuit 27 that works at the ocurrence of any abnormality, and a one-chip microcomputer circuit (shortened as MC circuit hereinunder) 28 that controls these circuits.

Figure 5:
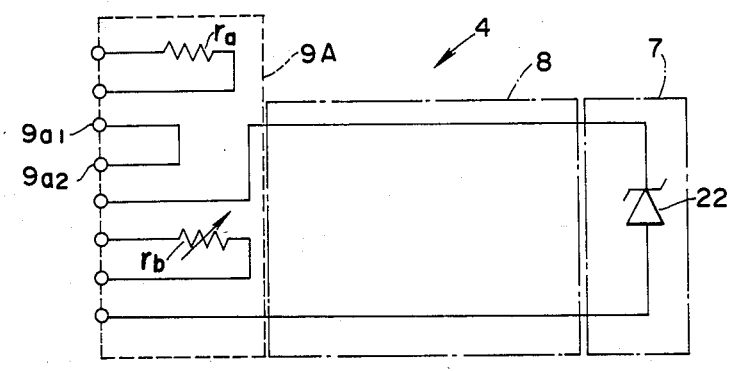
In FIG. 5 is shown the block diagram of equivalent circuit.

The above-mentioned constant current circuit 21 uses a constant voltage IC (for example, μA 723) 21a, applies the voltage of control output terminal Vout of this IC 21a to bias to the control collector emitter current of the control transistor 21b, and limits this current to a required value, for example, 540 mA and 400 mA, according to the diameters, large or narrow, of heater probe 4. For example, when a large-diametered heater probe 4 is applied, a resistance ra is connected to connector 9A, as shown in FIG. 5, and this resistance renders the current to Zener diode 22 higher than that which runs in a narrow-diametered heater probe. Namely, by this resistance ra, the composite resistance value of the emitter side of control transistor 21b in constant current circuit 21 becomes small and equal to the parallel resistance value of resistance 21r and resistance ra, and therefore, the limit current value becomes large. (The voltage between the both extremities of this resistance 21r is sensed by the constant voltage IC 21a (not illustrated)).

By adjusting the resistance value of a variable resistance rb which is mounted to the connector 9A, it is available to set an adequate current value even when Zener voltage Vz of Zener diode 22 varies.

The above-mentioned constant voltage IC 21a is equipped with a current limit terminal $C_{LIM}$ whereto a photo transistor 21CP$_1$ which forms a photo coupler is connected, and it turns on when light emitting diode (LED) 21Cd$_1$, the companion to this photo transistor 21Cp$_1$ lights, and the output power is then released from limitation. Light emitting diode 21Cd$_1$ which forms this photo coupler is connected from its anode to the supply terminal $V_A$ (+5 V) by way of a resistance, and the cathode thereof is connected, via inverter I$_1$ of an open collector, to the terminal C$_1$ of MC circuit 28 which functions as a control curcuit, and, when the voltage of this terminal C$_1$ becomes high (high level), LED 21Cd$_1$ lights. In addition, when the voltage of this terminal C$_1$ becomes high (high level), LED 24Cd, which is connected to inverter I$_1$ lights and photo transistor 24Cp installed in the minute constant current circuit 24, is turned on, and then the minute constant current is not output.

When photo transistor 21CP$_2$, which is connected to frequency correct terminal $F_{COM}$, is turned on, output current from the above-mentioned constant current circuit 21 is broken. LED 21Cd$_2$ which is the companion to this photo transistor 21Cp$_2$, is controlled by output level of terminal C$_2$ of MC circuit 28.

The voltage between the both extremities of the resistance 21r in the above-mentioned constant current circuit 21 is detected by broken wire detect circuit composed of operational amplifier 26a, (in the case where position between the contact points 23a and 23b which are indicated with dotted lines in the relay 23 is selected.). If the wire is broken, LED 26Cd lights and photo transistor 26Cp, the companion thereto, is turned on and a broken wire signal of low level is applied at the terminal C$_3$ of MC circuit 28 by way of buffer B$_1$.

In the above-mentioned MC circuit 28, when connector 9A is connected to connector receptacle 9B, the terminal C$_4$ changes from high level to low level by way of the terminals 9a$_1$ and 9a$_2$ whereto current is supplied from the connector 9A, and MC circuit 28 detects that the connector 9A of the heater probe 4 has been jointed. When this terminal $C_4$ thus changes to low level, the terminal $C_1$ changes to low level and LED 24C$d$ is turned off, photo transistor 24C$p$ is turned off and minute constant current circuit 24 then begins to function. In this case, the terminal $C_5$ is set for low level in the MC circuit 28 and transistor $Q_1$ which is connected thereto by the inverter $I_2$ is turned off and no current is delivered to the solenoid 23$s$ of the relay 23, and, under this condition, a current runs between the contacts 23$a$ and 23$c$ in the relay 23 as shown by a solid line, and therefore a minute constant current, for example 10 mA, is delivered from the above-mentioned minute constant current circuit 24, via connector 9A of heater probe, to Zener diode 22. This minute constant current circuit 24 is controlled so that the potential of on-load resistance 24$r$ is fed back via a resistance to the input of operational amplifier 24$a$ and a constant current (10 mA) is delivered to this on-load resistance 24$r$.

When the above-mentioned minute constant current is delivered, the cathode potential of Zener diode 22 is detected by the short-circuit deterioration detect circuit 25, and if this cathode potential has decreased below the permissible level (for example 19.9 V) that is determined by the resistances 25$r_1$ and 25$r_2$, the output of operational amplifier 25$a$ changes to the low level, LED 25C$d$ is turned on, the photo transistor 25C$p$ that is the companion thereto, is turned on, the terminal $C_6$ changes to the low level and qualitative deterioration or short-circuit is detected by MC circuit 28. The information as to whether this terminal $C_6$ is under an abnormal situation (low level) or under a normal condition (high level) is recorded by MC circuit 28, and, when the foot switch 5 is pushed under an abnormal condition, this MC circuit makes the alarm circuit 27 work, and it turns on the flash "WARNING" on the panel 2 and sounds a buzzer, which is different from that of normal heating, in order to warn the user, and it also control the heating current so that it will not go to the Zener diode 22.

(It is also possible to arrange to be warned of an abnormal situation as soon as the terminal $C_6$ changes to the low level even if the foot switch 5 is not pushed.)

Under the condition that the above-mentioned terminal $C_6$ is ready for high level, when the foot switch 5 is pushed, the terminal $C_5$ changes to high level, drives the solenoid 23$s$ of the relay 23 by way of inverter $I_2$ and transistor $Q_1$, turns off the contacts 23$a$ and 23$c$ that "ON", and connects electrically contacts 23$a$ and 23$b$, and changes the output of terminal $C_2$ to low level, makes LED 21C$d_2$ flash, turns of photo transistor 21C$p_2$, makes the constant voltage IC 21$a$ work and supplies a current to Zener diode 22. If there is a disconnection in the heater probe 4, no current flows, and therefore the potential difference between the two extremities of resistance 21$r$ should be detected by the use of operational amplifier 26$a$. However, if there is a disconnection, the output level of this operational amplifier 26$a$ changes to high level, LED 26C$d$ flashes, the terminal $C_3$ changes to high level, this abnormality is supplied to MC circuit 28 and the alarm circuit 27 warns the user of the abnormality. On the other hand, when the current can be delivered, the above-mentioned output level of operation amplifier 26$a$ becomes a low level. Therefore, terminal $C_3$ is low level while the current is being supplied, and when a discontinuity occurs while Zener diode 22 is being heated, this terminal $C_3$ becomes high level and the accident of a discontinuity can be detected.

Since the heating period (time) on the Zener diode 22 is set previously by the use of the setting button 2$b$ on the panel 2, it is possible to detect whether any discontinuity might have occurred, or not, by detecting whether terminal $C_3$ would become high level before the signal period.

The operation of the second embodiment thus composed is explained hereinunder.

When connector 9A of heater probe 4 is connected to connector receptacle 9$b$ of power box 3, terminal $C_4$ of MC circuit 28 is set for low level through the intermediary of terminals 9$a_1$ and 9$a_2$ and the connection of connector 9A is detected. When this connection is detected, MC circuit 28 sets terminal $C_1$ for low level, makes LED 24C$d$ flash, turns off photo transistor 24C$p$, actuates minute constant current circuit 24$a$, and supplies minute constant current from terminal 9 Hp to heater probe 4. (In this case, terminal $C_5$ is set for low level, contacts 23$a$ and 23$c$ are electrically connected in relay 23). Then, operational amplifier 25$a$ detects the cathode potential of Zener diode 22 as to whether, or not, it is below the permissible level, and short-circuit or deterioration as to whether, or not, there is a short-circuit of the heater probe 4. Thus, in the presence of short-circuit or qualitative deterioration, when foot switch 5 is pushed for heating the heater probe 4, this amplifier warns of such abnormality as a short-circuit or qualitative deterioration, and it interrupts the current to the heater probe 4.

In the absence of the above-mentioned abnormality, when the foot switch is pushed for heating the heater probe 4, terminal $C_5$ of MC circuit 28 is set for high level, turns on transistor $Q_1$, actuates relay 23 and connects electrically contacts 23$a$ and 23$b$, and, at the same time, sets the terminal $C_2$ for low level, turns off photo transistor 21C$p_2$, actuates the constant voltage IC 21$a$, and supplies a current for heating to the Zener diode 22 via collector emitter and resistance 21$r$ of control transistor 21$b$, contacts 23$b$ and 23$a$ and terminal 9 Hp. If there is a disconnection of the heater probe side, no current is supplied and no potential difference arises, and this condition is therefore detected by the operational amplifier 26$a$.

Namely, in the presence of a disconnection, the output of operational amplifier 26$a$ becomes high level, LED 26C$d$ flashes, photo diode 26C$p$ which is the companion thereto is turned off, the terminal $C_3$ becomes high level via buffer $B_1$, and the alarm circuit warns of the presence of the disconnection as an abnormality. On the other hand, in the absence of a disconnection, current is supplied to Zener diode 22 and, in this case, the output of the operational amplifier is low level, LED 26C$d$ flashes and the terminal $C_3$ is kept at low level. Even when a disconnection occurs while the Zener diode 22 is being heated, the disconnection is detected and it can be warned of by the alarm circuit 27.

In the above-mentioned second embodiment when the connector 9A is not connected, the terminal $C_4$ of the MC circuit 28 is set for high level, the relay 23 connects contacts 23$a$ and 23$c$ and, therefore a power supply line for heating is not formed. Simultaneously, the terminal $C_1$ becomes high level, the photo transistor 24C$p$ is turned on and the minute constant current circuit 24 is maintained not to supply minute current, and the terminal $C_2$ changes to low level, the photo transistor 21C$p_2$ is turned on, and the constant voltage IC 21 functions not to output heating power to the Zener diode 22. Therefore, even when the operator touches the connector 9A with a wet hand, he does not receive an electric shock and can use the unit safely.

According to the second embodiment that functions as mentioned above, the unit has a means to detect various troubles and, therefore, it will not be misoperated and can be used without fear.

What we mentioned above is no more than one of the possible embodiments of this invention, and various other embodiments may also be possible. For example, a semiconductor such as a transistor, thryistor, etc. may be used instead of relay 23 as a means for changeover and, in such a case, it is possible to add a means which is able to detect the condition of such a semi-conductor in order to assure safety.

In the above-mentioned second embodiment, MC circuit 28 is used as a means for control, but the control means is not limited to this circuit, and means may be used to actuate a circuit which functions directly according to the output signal of various detection means.

Any unit which has at least one of the above-mentioned means to detect such troubles as above-mentioned belongs to this invention.

Detection of a discontinuity by checking the cathode potential in the same way as the short-circuit or deterioration detection circuit may be used as well.

As mentioned up to here, according to the second embodiment, the unit of this invention has various means to detect troubles such as a heater probe connection detection means, heater probe short-circuit or deterioration detect means, discontinuity detect means, etc. and it is prepared to warn of various abnormalities, and therefore it is able to prevent misoperation and to improve the safety of a cautery hemostatic unit.

Figure 6:
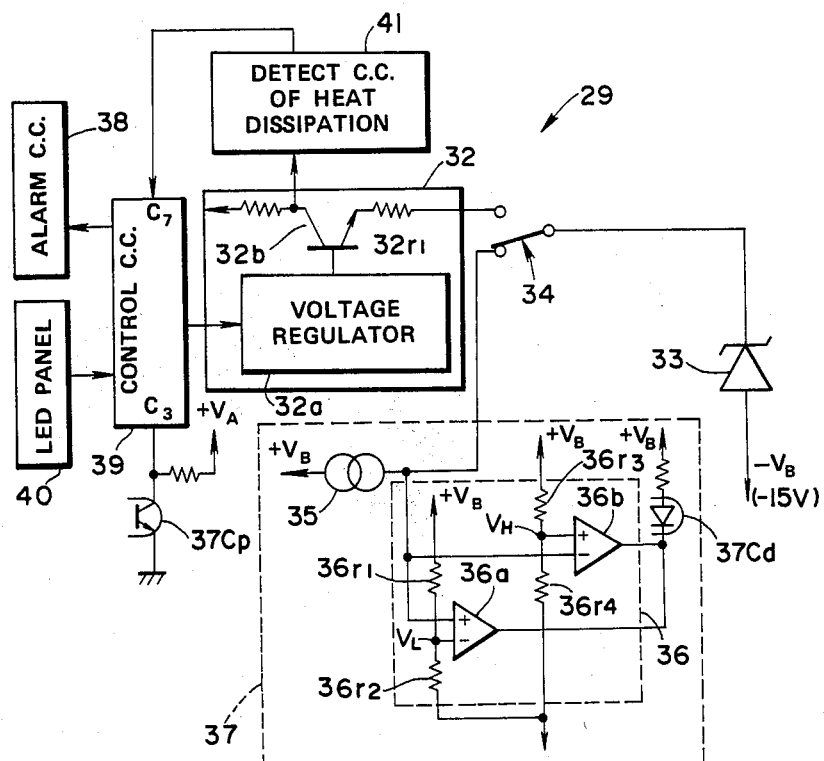
In FIG. 6 is shown the block diagram that shows the outline composition of the probe drive circuit in a third embodiment of this invention.

In FIG. 6 is shown the composition of the main part of a probe drive circuit 29 in the third embodiment of this invention.

This probe drive circuit 29 has a property detection circuit 37 and is composed of a drive constant current circuit 32a, Zener diode 33 as a thermal element to which the drive constant current circuit 32 supplies a constant current and a comparator circuit 36 that supplies a minute constant current to the Zener diode 33 from minute constant current circuit 35 when switched over by switch 34, and, under this condition, takes the voltage, for example, of the cathode of the Zener diode 33 and compares it with a fixed comparison voltage, a control circuit 39 that actuates the alarm circuit 38 that takes the detection output from the property detection circuit 37, keeps the whole unit working according to the detection output and warms of deterioration etc., and a heat dissipation detection circuit 41 that detects heat dissipation displayed on LED panel 40.

The above-mentioned control circuit 39 works to control not only the detection of deterioration of Zener diode 33, but also to control a LED panel 40 that flashes or goes out according to the content of an operation set by the use of the setting buttons 2a and 2b on the panel 2 mentioned before, and the time constant parameter of heat dissipation detection circuit 41 according to the above-mentioned content of operation, etc.

As the above-mentioned Zener diode 33, which is made of a material where Zener voltage is about 20 V and has a maximum rating of 5 W. The anode of this Zener diode 33 is connected to a negative delivery end $-V_B$ ($V_B$ = 15 V). However, when used, the cathode of Zener diode 33 is connected to the drive constant current circuit 32 by switch 34 and the cathode thereof is connected via resistance 32 $r_1$ to the emitter of control transistor 32b that is controlled by constant voltage IC 32a of drive constant current circuit 32.

On the other hand, before and after use, (the cathode of) Zener diode 33 is connected to the property detect circuit 37 by switch 34, and, under the condition that a constant current of about 10 mA is supplied from the above-mentioned minute constant current circuit 35, comparator 36a detects whether the cathode voltage of Zener diode 33 (voltage to negative delivery end potential $-15$ V) is, for example, above 18 V, or comparator 36b detects whether it is, for example under 25 V.

When the voltage of the above-mentioned Zener diode 33 is within the permissible range, the output of both comparators 36a and 36b changes to high level, photo diode 37Cd does not flash, photo transistor 37Cp that forms a photo coupler with photo diode 37Cd is off and the potential of the connector thereof is maintained at high level. On the other hand, when the cathode potential of Zener diode 33 shifts to the low side or to the high side out of the permissible range, the output, either of comparator 36a or of comparator 36b, changes to low level, photo diode 37Cd flashes and the collector potential of photo transistor 37Cp changes to low level. This low level potential is detected by the terminal $C_6$ of control circuit 39 and alarm circuit 38 warns of the necessity to replace Zener diode 33.

Figure 7:
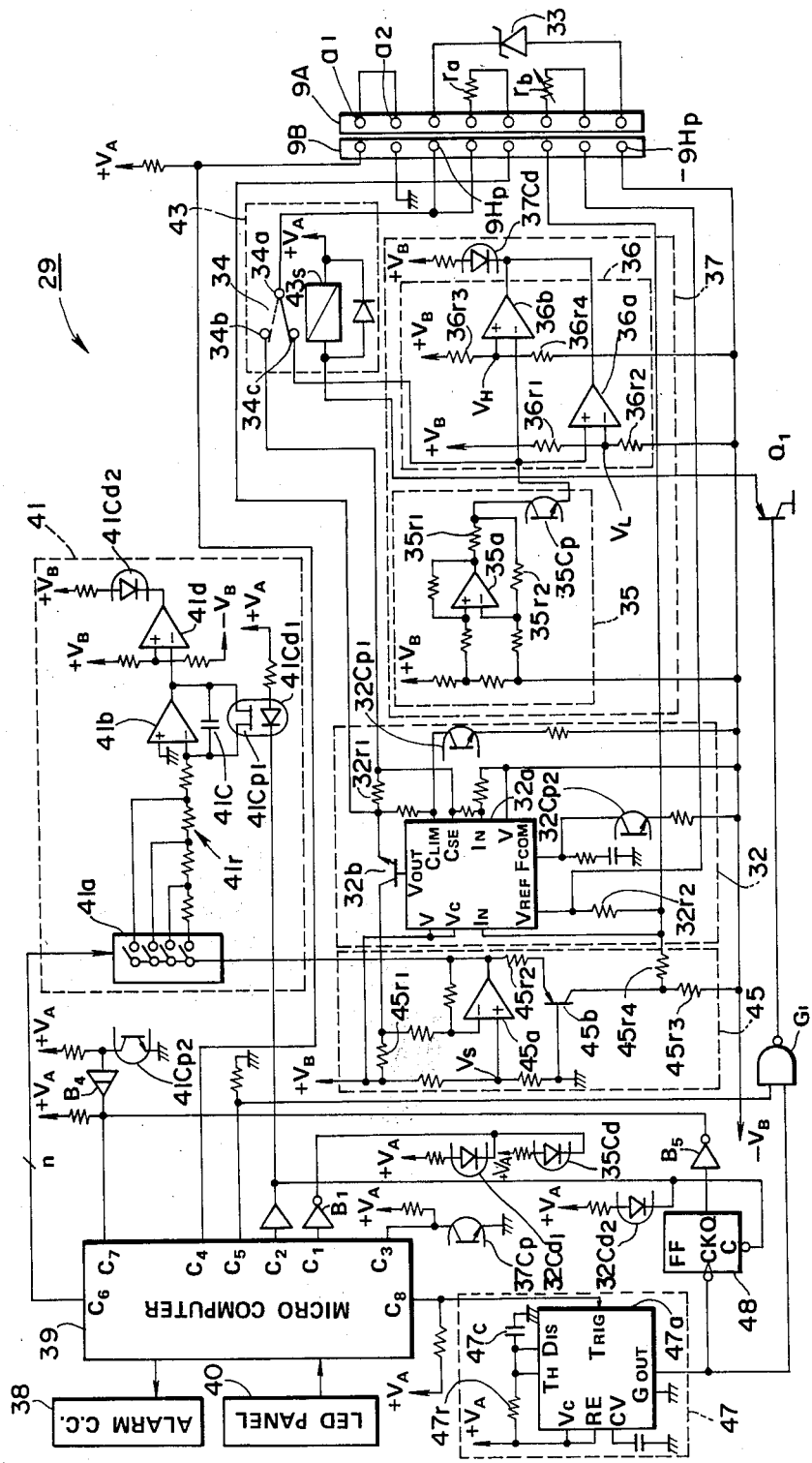
In FIG. 7 is shown the block diagram of the concrete composition of the probe drive circuit in the third embodiment.

FIG. 7 shows the concrete circuit composition of the above-mentioned probe drive circuit 29.

The probe drive circuit 29 has, as mentioned before, a drive constant current circuit 32, a Zener diode 33 as a thermal element whereto this drive constant current circuit 32 supplies a constant current, a minute constant current circuit 35 that changes over the switch 34 at relay 23 and supplies a minute constant current (for example 10 mA) to the Zener diode 33 in order to detect the qualitative deterioration of Zener diode 33, a property detect circuit 37 that, while this constant current is supplied, detect whether, or not, the cathode potential of Zener diode 33 is within the permissible range or whether, or not, there is a short-circuit or a disconnection, an alarm circuit 38 that functions in the presence of a functional abnormality of trouble, a heat dissipation detection circuit 41 that detects whether, or not, the total heat dissipation has reached a set value, and, in addition, a heat control circuit 45 for controlling the heating temperature of the above-mentioned Zener diode 33 by utilizing the temperature dependency of Zener voltage Vz, a time measuring circuit that measures time from the moment of supply of current for heating to the above-mentioned Zener diode 33 and composed of a current interrupting means which changes over switch 34 of relay 43 by an output signal thereof and can interrupt the output current forcedly, and these circuits are controlled by control circuit 39 that is formed with a one chip micro computer.

The above-mentioned drive constant current circuit 32 uses a constant voltage IC (for example, $\mu$A 723) 32a, applies the voltage of control output end Vout thereof at the base and controls collector emitter current of control transistor 32b and is able to limit current to the required current value, for example 540 mA or 400 mA, according to the diameters of heater probes, a large-diametered one or a small-diametered one.

To current limit terminal $C_{LIM}$, photo transistor 32$C_{p1}$ is connected and when LED 32$C_{d1}$ that is the companion thereof lights, this current limit terminal and this photo transistor are electrically connected, then the output current is released from limitation. The anode of this LED 32C$d_1$ is connected, via a resistance, to (positive) delivery end $V_A$ (+5 V), and the cathode thereof is connected to the terminal $C_1$ of control circuit 39 via buffer $b_1$ by inserter of open collector and, when this terminal $C_1$ changes to high level, LED 32C$d_1$ flashes.

In the above-mentioned drive constant current circuit 32, when photo transistor 32C$p_2$ that is connected to frequency correcting terminal COM is turned on, output current of drive constant current circuit 32 is broken. LED 32C$d_2$ that is the companion thereto is controlled by the output level of terminal $C_2$ of control circuit 39.

In the above-mentioned control circuit 39, when connector 9A is connected to connector receptacle 9B, the terminal $C_4$ changes, for example, from high level to low level via the terminals $9a_1$ and $9a_2$ whereto current is supplied at connector 9A, and control circuit 39 is able to detect that connector 9A of heater probe 4 is connected. When terminal $C_4$ changes to low level, the control circuit 39 makes the terminal $C_1$ change to high level, makes LED 35C$d$ flash, turns on photo transistor 35C$p$ and actuates minute constant current circuit 35. In this case, the terminal $C_5$ in the control circuit 39 is set for low level, transistor $Q_1$ via (nand) gate $G_1$ is off and no current is delivered to solenoid 43$s$ of relay 43 and, under this situation, current is delivered between contact 34$a$ and contact 34$c$ in switch 34 as shown by a solid line and, therefore, a minute constant current, for example 10 mA, is supplied from the above-mentioned minute constant current circuit 35 to Zener diode 3 via connector 9A of heater probe 4. The minute constant current circuit 35 feeds back the voltage of on-load resistance 35$r_1$ at resistance 35$r_2$ through operational amplifier 35$a$, and is controlled so that a fixed current (10 mA) can be fed to the resistance 35$r_1$ thereof.

When the above-mentioned minute constant current is supplied, the cathode potential of Zener diode 33 is detected by the property detection circuit 37.

Namely, the reverse input end of comparator 36$a$ in comparison circuit 36 is set so that the voltage $V_L$, that is obtained by dividing +$V_B$ and −$V_B$ by resistances 36$r_1$ and 36$r_2$ (+18 V to −$V_B$; +3 V to 0 level) is supplied, and the cathode voltage of Zener diode 33 is supplied on the non-reverse input. The comparator 36$b$ is set so that the voltage $V_H$ obtained by dividing non-reverse input +$V_B$ AND −$V_B$ by resistances 36$r_3$ and 35$_6$ (+25 V to −$V_B$) is supplied, and the above-mentioned cathode potential is supplied to the non-reverse input.

The outputs of these comparators, 35$a$ and 36$b$, are connected to delivery +$V_B$ by way of LED 37C$d$ and a resistance. (It is also possible to connect the outputs of these comparators, 36$a$ and 26$b$, via a resistance without connecting it directly.) And it is also possible to connect a (Zener) diode to a forward resistance and a backward resistance for protection of comparators 36$a$ and 36$b$ which are connected in parallel. It is possible to use this output in an other circuit, when there is a large input potential difference between the input of comparator 36$a$ and that of comparator 36$b$. Therefore, when a Zener diode has the correct Zener voltage Vz at a constant current of 10 mA, the outputs of these comparators 36$a$ and 36$b$ are high level and LED 37C$d$ does not flash. However, when Zener voltage Vz becomes different from the above-mentioned proper value due to qualitative deterioration during use, etc. the output either of comparator 36$a$ or comparator 36$b$ changes to low level and LED 37C$d$ flashes. When this LED 37C$d$ flashes, photo transistor 37C$p$ is turned on and the terminal $C_3$ changes from high level to low level. When this terminal $C_3$ changes to low level, control circuit 39 detects a qualitative abnormality and actuates alarm circuit 38, which then warns that the property of Zener diode 33 is out of permissible range and of the necessity of replacement thereof. Also when a Zener diode which is newly mounted for replacement is far from the standardized value, even not due to qualitative deterioration thereof, the alram circuit 38 informs the user that the used Zener diode is not suitable.

The collector of control transistor 32$b$ is connected to the feed for heating $V_B$ (+15 V) via resistance 45$r_1$ (in the heat control circuit 45), and the voltage drop due to this resistance 45$r_1$ is supplied at one of the two inputs of operation amplifier 45$a$, and the standard potential Vs is held at the other input thereof. This operational amplifier amplifies the voltage between these two inputs 3.9 times, and this output is supplied at the input of multiplexor 41$a$ of heat dissipation detection circuit 41 and is also transferred to negative feed −$V_B$ via resistance 45$r_2$, emitter collector of transistor 45$b$ and resistance 45$r_3$.

By this current, the potential changes at the contact between resistance 45$r_3$ and collector of transistor 45$b$, and the potential changes the voltage of (non-reverse) control input $I_N$ of constant voltage IC 32$a$ by way of resistance 45$r_4$, the voltage of the control input $I_N$ changes the output level of control output Vout, and current for heating is controlled. In this case, the feedback loop is set to be a positive feedback. For example, when current which passes resistance 45$r_1$ is amplified, the potential of non-reverse input falls and, thereby, the output level of operational amplifier 45$a$ elevates, the collector potential of transistor 45$b$ also elevates, the potential of control input $I_N$ of constant voltage IC 32$a$ is also increased, the output level of control output Vout also increases and current for heating, which flows in control transistor 32$b$, is amplified. By contrast, current for heating decreases.

The above-mentioned control input and $I_N$ is connected to the reference voltage $V_{REF}$ via resistance 32$r_2$.

On the other hand, in the above-mentioned heat dissipation detection circuit 41, the combination in which the series resistance 41$r$ (four resistances are illustrated in FIG. 7) are connected is available by digital signal from the terminal(s) $C_6$ of control circuit 39 and it is possible to select the series composite resistance value thereof. It is possible to select the integration time constant of the IC by this composite resistance and the capacitance of condenser 41C that is connected between the reverse input and the output of operational amplifier 41$b$. Both ends of condenser 41C of operational amplifier 41$b$ that composes the above-mentioned IC are connected to photo FET 41C$p_1$, and, that the condition that LED 41C$d_1$ flashes, both ends of condenser 41C are connected to each other, and the output of operational amplifier 41$b$ is kept to be lower than the level of non-reverse input of operational amplifier 41$d$.

When the terminal $C_2$ of the above-mentioned control circuit 39 is changed to high level, the condenser 41C is released from short-circuit and the integration function begins, and when the output of operational amplifier 41$b$ becomes lower than the reference level in the subsequent operational amplifier 41$d$, the output of operational amplifier 41d decreased to low level and LED 41C$d_2$ goes out. However, when this LED 41C$d_2$ lights, photo transistor 41C$p_2$ that is the companion thereto is turned on, and the terminal $C_7$ is changed to low level via buffer $B_4$. When this terminal $C_7$ changes to low level, the control circuit 39 makes, for example, the terminal $C_2$ change to low level and actuates LED 32C$d_2$ to flash, turns on photo transistor 32C$p_2$ to interrupt current output to the on-load side from drive constant current circuit 32.

If short-circuit or qualitative deterioration is not detected after supplying minute constant current in spite of electric connection between the contacts 34a and 34c of switch 34 in relay 43, the foot switch 5 can be pushed. The terminal $C_8$ will then change to low level from high level and a trigger signal is output. This signal is supplied at trigger input $T_{RIG}$ of the IC for timer 47a (for example, NE555) that forms the time measure circuit, and this IC for the timer outputs a high level signal from the output OUT for a period of time (for example 10 seconds) set by condenser 47c from the rise of this trigger signal, and this output signal is applied at gate $G_1$ and also at clock terminal CK of flip-flop 48. The flip-flop 48 is ready to output a low level signal, which becomes a signal level for stopping the output, to the terminal $C_7$ of control circuit 39 from output end Q at the rising edge of the clock signal. Namely, due to this means for stopping output, even when a disconnection occurs in heater probe 4 during use, the terminal $C_7$ is changed forcedly by output from time measure circuit 47 via this flip-flop 48, and, therefore, control circuit 39 changes the terminal $C_2$ to low level in the same way as when the IC works normally by the heat dissipation detection circuit, and functions so that current for heating is not output. Even if control circuit 39 runs away due to external noise, etc., the output of IC for timer 47a falls to low level after a fixed time, and therefore transistor $Q_1$ via gate $G_1$ is turned off and switch contacts 34a and 34b of relay 43 are switched off and the power feed line is not formed.

Consequently, even if the control circuit 39 runs away etc., the power feed line of relay 43 is turned off at the switch contacts 34a and 34b by time measure circuit 47 using the IC for timer 47a, flip-flop 48 which functions by output from this time measure circuit 47, gate $G_1$, and therefore it is possible to prevent the continuation of current supply to Zener diode 33.

In the case that the control circuit 39 works normally when the terminal $C_7$ changes to low level, the above-mentioned switch contacts 34a and 34b are turned off, and, by changing the terminal $C_2$ to low level, output current from the constant voltage IC 32a is interrupted.

The heat control circuit 45 controls the heating temperature of Zener diode 33 in the following way.

Namely, in a Zener diode 33 used as a thermal element, the Zener voltage Vz thereof has a minute positive temperature dependency, and when it is heated thereby, the temperature elevation various dependently upon the heat radiation from the distal extremity 7 of heater probe 4, and the change in current due to this phenomenon is detected, as potential falls at resistance 45$r_1$, by the operational amplifier 45a, and by the positive feedback loop including this operational amplifier 45a, the above-mentioned current is controlled. Namely, when temperature rise becomes large, current decreases in order to prevent excessive elevation of temperature at the distal extremity 7, and when heat radiation is large, the caloric value become large, in order to keep adequate temperature for hemostasis.

We hereunder explain the functions of the third embodiment that is composed as above-mentioned.

When connector 9A of heater probe 4 is connected to connector receptacle 9B of power box 3, the terminal $C_4$ of control circuit 39 changes to low level via terminals 9$a_1$ and 9$a_2$, and the connection of the connection 9a is thus detected. When this connection is detected, the control circuit 39 sets the terminal $C_1$ for high level, makes LED 35C$d$ flash, actuates the minute constant current circuit 35 by turning on photo transistor 35C$p$ and supplies minute current to the Zener diode 33. In this case, since transistor $Q_1$ is turned off when the terminal $C_5$ changes to low level, the switch contacts 34a and 34c are "ON" in the relay 43. Thus, by both comparators 36a and 36b, it is detected whether the cathode potential of Zener diode 33 is within the permissible range and whether there is a short-circuit in the heater probe 4. (In addition to detection as the whether Zener voltage Vz of the above-mentioned Zener diode 33 is within the permissible range, short-circuit in Zener diode 33 is detected by comparator 36a and disconnection is detected by comparator 36b, and, therefore, not only qualitative deterioration, but also the presence of absence of a short-circuit or disconnection is detected.).

In the above-mentioned minute constant current circuit 35, the resistances 35$r_1$ and 35$r_2$, etc. are set so that, at unloading, the voltage between the terminal 9 Hp whereto Zener diode 33 is connected and $-9$ Hp is almost 30[V] and the terminal of emitter of photo transistor 35C$p$ (when turned on) is almost 15 V (more precisely, 15.1 V). Therefore, $(30-V_E)/R_{35r1} = V_E/R + (V_E-15)/R_{35R2}$, wherein Ve is the voltage of the above-mentioned terminal 9 Hp, and R is the on-load resistance between the terminal 9 Hp and the terminal $-9$ Hp, and $R_{35r1}$, and $R_{35r2}$, are resistance values of resistances 35$r_1$ and 35$r_2$, respectively. Consequently, when the Zener diode is connected as the above-mentioned load, the current value is 9, 9–10 and 7[mA] for Zener voltages of 19, 3–20 and 1 [V], respectively, and it is thus possible to examine the property of this Zener diode under conditions equivalent to the requirements concerning the product standards established by manufacturer.

When a current is supplied to Zener diode 33, the Zener voltage Vz thereof increased apparently.

As a matter of fact, the temperature increases most immediately after supply of a large current for heating. Therefore, it is necessary to take into account such an increase in Zener voltage Vz due to such temperature elevation, when measuring after use.

When room temperature is 25° C., the maximum temperature of the Zener diode at the distal extremity will be 225° C. at heating; i.e. the temperature increases by 200° C. The temperature coefficient of Zener voltage Vz of a Zener diode beng 15 mV/° C., the increase in Zener voltage for an increase by 200° C. is: 15 mV×200° C.=3 V.

Therefore, the threshold can be set by adding 3 V to the upper limit of the normal selection range. In practice, $-9$ Hp is regarded as the base and 25 V is set as the upper limit of the threshold, because of error in the operational amplifier. As to the lower limit of threshold, it is possible to take the lower limit of Zener voltage Vz of a Zener diode 33 that is incorporated in the distal extremity, because the temperature coefficient of Zener voltage Vz is positive, but, taking possible variation into consideration, 18 V is set as the lower limit. Therefore, an output signal that is judged as normal for probe 4 is one which is within 18–25 V, including temperature elevation due to heating current or detection current. In the absence of qualitative deterioration, when foot switch 5 is pushed, the terminal $C_5$ is changed to high level and the constant voltage IC 32a functions and, at the same time, relay 43 turns on switch contacts 34a and 34b and forms a power feed line and current for heating is then supplied to the Zener diode 33.

The above-mentioned terminal $C_5$ is changed to high level and the terminal changes to low level for a certain time, for example 10s mS. It is possible to form this period of time by the use of built-in time measuring means of control circuit 39 or the IC for timer. At the rising edge of the voltage at terminal $C_8$ from low level to high level, the output of timer IC of time measure circuit 47 is high level for a certain time, and this output is applied at the other input of gate $G_1$.

After delay action time (10s mS) of the above-mentioned relay 43, (it is also possible to set this delay time by the use of a clock incorporated in the control circuit 39 or timer IC, etc.), the control circuit 39 changes the terminal $C_2$ to high level, turns off LED 32C$d_2$, switches off photo transistor 32C$p_2$ and allows current to flow to the Zener diode 33, and at the same time, it turns off LED 41C$d_1$ and actuates IC composed of operational amplifier 41b, etc.

Current to the Zener diode 33 is amplified (for example, to about 1.5 A) by the positive feedback loop using operational amplifier under a condition free from current limitation, and Zener diode 33 is very rapidly heated, and 150 mS after heating, an elapsed-time signal is input in control circuit 39, which then changes terminal $C_1$ to low level. When this terminal changes to low level, LED 32C$d_1$ goes out and current flow to Zener diode 33 is limited.

Since Zener voltage Vz of the above-mentioned Zener diode 33 has temperature dependence, the more the temperature rises, the less current flows. The decrease of current is detected by the heat dissipation detection circuit, the positive feedback loop controls the circuit so that the in increase of temperature is limited, and therefore the temperature is kept at a level suitable for hemostasis even when heat radiation varies at the distal extremity 7.

Current flowing to the Zener diode 33 is integrated by IC by way of multiplexor 41a, and when the caloric value reaches the previously set value, the output of operational amplifier 41d changes to high level, LED 41C$d_2$ is turned off, photo transistor 41CP$_2$ is turned off, terminal $C_7$ changes to low level and interruption in made.

Then, control circuit 39 changes the signal level of terminals $C_2$ and $C_5$ to low level.

When terminal $C_2$ is changed to low level, LED 32C$d_2$ lights, photo transistor 32C$p_2$ is turned on and heating current is not output from the drive constant current circuit 32. When terminal $C_5$ is changed to low level, one of the input of gate $G_1$ is changed to low level and, therefore, transistor $Q_1$ is turned off and the relay 43 turns off swtich contacts 34a and 34b in order not to form a power feed line. Thus, heating is stopped. The output of timer IC 47a changes to low level after a certain period of time.

The above-mentioned function is the case where the control circuit works normally. In presence of disconnection in heater probe 4, the control circuit 39 may sometimes run away due to external noise, etc. or, otherwise, no signal may be output from the heat dissipation detect circuit 41. Even in such cases, after a certain period of time, the output of timer IC 47a falls to low level, and , therefore, in the same manner as above mentioned, transistor $Q_1$ via gate $G_1$ is turned off, the relay 43 opens the switch contact 34a and 34b to break heatng current. At the rising edge of above-mentioned low level, the output of flip-flop 48 changes to high level and terminal $C_2$ is changed to low level and then interruption as above-mentioned is made. Therefore, even if control cirucit 39 or other parts work in a wrong way, heatng current is certainly stopped by the time measure means after some time and the unit can be safely used without abnormally heating the bleeding site.

It is possible to form a means to interrupt forcedly the heating current such as is done by the time measure means not only with relay 43 but also with a semi-conductor such as a thyrister, etc.

In the case of detection of qualitative change of the Zener diode (including short-circuit, disconnection, etc.) by the use of the above-mentioned property detect circuit 37, it is preferable to operate this circuit 37 before and after use for stopping hemorrhage. In this case, it is not necessary to operate it for long period of time, and, in the third embodiment, it is possible to control it freely until the photo transistor 35C$p$ is turned on. Even during use for cautery hemostasis, it is possible to run the property detection circuit 37 while the heating as cautery hemostatic is being stopped.

It is also possible to set it to warn of the presence of troubles in the thermal element when an abnormality (disconnection, short-circuit, etc.) occurs due to installation of comparators whereby different levels from those set by the comparators 36a and 36b are generated in the comparison circuit 36 of the above-mentioned property detect circuit 37.

As mentioned up to here, according to the third embodimemt. this invention has means to detect short-circuits due to qualitative deterioration of the thermal element, disconnection thereof, etc., and permits detecting them under the same conditions as the manufacturer's product standards, and it is therefore possible to detect the degrees of qualitative deterioration more certainly. Thus, this invention permits improvement in the reliability of cautery hemostatic unit.

It is clear that this invention permits various embodiments in application to many different fields without departing from its spirit and scope.

Except what we claim in the attachment, the invention may be applied for any purpose.

What we claim is:

1. A cautery hemostatic unit comprising:
    a power box;
    slender probe means which is deliverable through an insert channel of an endoscope, said probe means having a distal extremity end and a proximal extremity end;
    connector means for connecting said proximal extremity end of said probe means to said power box;
    a semi-conductor thermal element of small heat capacity contained in said distal extremity end of said probe means, said thermal element having a first and second end;
    constant current circuit means for supplying a constant current to electrically heat said thermal element when said probe means is connected to said connector means to said power box;

setting button means on said power box for selecting and setting an amount of heat to be generated by said thermal element to heat tissue when said distal extremity end of said probe means is applied to said tissue;

heat dissipation detection means connected to said setting button means for detecting whether the amount of heat generated by said thermal element selected by said setting button means is achieved;

minute current circuit means for detecting deterioration of said thermal element, said minute current circuit means being connected to said thermal element for supplying a minute constant current to electrically test said thermal element, said minute current circuit means being connected to said thermal element when (a) said heat dissipation detection means detects said amount of heat set by said setting button means and generated by said thermal element has been achieved so that constant current is absent from said thermal element and (b) said thermal element is connected by said connector means to said power box;

changeover means for detecting an abnormality, said changeover means switching said thermal element from said minute current circuit means to said constant current circuit means in order to detect a characteristic deterioration of said thermal element;

a changeover control means to control the switching function of said changeover means from said minute constant current of said minute current circuit means to the constant current of said constant current circuit means, said changeover control means causing said minute constant current to be supplied to said thermal element only before said constant current is supplied to said thermal element;

recognition circuit means connected to said constant current circuit means and said minute current circuit means for providing an output which indicates whether a voltage between said first and second ends of said thermal element is within a predetermined range either when said constant current is applied to said thermal element or when said minute constant current is applied to said thermal element; and an alarm circuit means connected to said output of said recognition circuit means, said alarm circuit means functions according to said output of said recognition circuit.

2. A unit, as mentioned in claim 1, which has a property deterioration detect means which detects qualitative deterioration of said thermal element by detecting whether the voltage of said first and second ends of said thermal element is within a predetermined range when said minute constant current is supplied to said thermal element from said minute constant current circuit means by said changeover means.

3. A unit, as mentioned in claim 2, which is equipped with a connection detect means to detect connection of said probe means to said connector means.

4. A unit, as mentioned in claim 2, which possesses a disconnection detect means to detect whether there is a disconnection, or not, according to the potential difference between the first and second ends of a resistance arranged in series with said thermal element when switched over to supply heating constant current to said thermal element.

5. A unit, as mentioned in claim 2, wherein said property deterioration detect means detects the qualitative deterioration of said thermal element by comparing the voltage level at one of said first and second ends of said thermal element with a reference level.

6. A unit, as mentioned in claim 2, wherein said property deterioration detect means detects the qualitative deterioration of said thermal element by comparing one of said first and second ends of said thermal element with two different reference levels.

7. A unit, as mentioned in claim 2, which has a heating time limit means to interrupt said heating constant current circuit means after a maximum heating time.

8. A unit, as mentioned in claim 2, further including a heat control means to keep a heating temperature of said thermal element at a constant level according to the change in voltage which corresponds to the increase in temperature of said thermal element when heating constant current is supplied to said thermal element.

9. A unit, as mentioned in claim 8, wherein said heat control means controls said heating temperature of said thermal element according to the output of a comparator which compares a reference value and one of a first and second end of a resistance which is connected in series with said thermal element wherein the fall of voltage between the input and said output of said comparator is temperature-dependent.

* * * * *